US008383103B2

(12) United States Patent
Gaylis et al.

(10) Patent No.: US 8,383,103 B2
(45) Date of Patent: Feb. 26, 2013

(54) BOTULINUM TOXIN COMPOSITIONS AND METHODS

(75) Inventors: Franklin D. Gaylis, La Mesa, CA (US); Andrew M. Blumenfeld, Del Mar, CA (US)

(73) Assignees: Allergan, Inc., Irvine, CA (US); Franklin D. Gaylis, La Mesa, CA (US)

( * ) Notice: Subject to any disclaimer, the term of this patent is extended or adjusted under 35 U.S.C. 154(b) by 486 days.

(21) Appl. No.: 12/032,057

(22) Filed: Feb. 15, 2008

(65) Prior Publication Data

US 2008/0199453 A1 Aug. 21, 2008

Related U.S. Application Data

(60) Provisional application No. 60/890,052, filed on Feb. 15, 2007.

(51) Int. Cl.
*A61K 38/46* (2006.01)
(52) U.S. Cl. ............... 424/94.62; 424/94.6; 424/94.63; 424/94.67; 424/236.1; 424/239.1; 424/247.1
(58) Field of Classification Search ................. None
See application file for complete search history.

(56) References Cited

U.S. PATENT DOCUMENTS

| | | | | |
|---|---|---|---|---|
| 5,437,291 | A | 8/1995 | Pasricha | 127/898 |
| 5,670,484 | A | 9/1997 | Binder | 514/14 |
| 5,714,468 | A | 2/1998 | Binder | 514/14 |
| 5,766,605 | A | 6/1998 | Sanders | 424/239.1 |
| 5,861,431 | A | 1/1999 | Hildebrand et al. | 514/557 |
| 6,063,768 | A | 5/2000 | First | 514/14 |
| 6,139,845 | A | 10/2000 | Donovan | 424/236.1 |
| 6,265,379 | B1 | 7/2001 | Donovan | 514/14 |
| 6,296,867 | B1 | 10/2001 | Gokcen et al. | 424/94.2 |
| 6,299,893 | B1 | 10/2001 | Schwartz | 424/422 |
| 6,306,423 | B1 | 10/2001 | Donovan | 424/423 |
| 6,312,708 | B1 | 11/2001 | Donovan | 424/423 |
| 6,358,926 | B2 | 3/2002 | Donovan | 514/14 |
| 6,365,164 | B1 | 4/2002 | Schmidt | 424/239.1 |
| 6,423,319 | B1 | 7/2002 | Brooks | 424/239.1 |
| 6,458,365 | B1 | 10/2002 | Aoki | 514/2 |
| 6,464,986 | B1 | 10/2002 | Aoki | 514/2 |
| 7,449,192 | B2 | 11/2008 | Schmidt | |
| 7,455,845 | B2 | 11/2008 | Schmidt | |
| 7,470,431 | B2 | 12/2008 | Schmidt et al. | |
| 7,538,097 | B2 | 5/2009 | Frost | |
| 7,544,499 | B2 | 6/2009 | Frost | |
| 2002/0025327 | A1 | 2/2002 | Schmidt | 424/239.1 |
| 2003/0113349 | A1 | 6/2003 | Coleman | |
| 2004/0067235 | A1 | 4/2004 | Doshi | 435/6 |
| 2005/0260186 | A1 | 11/2005 | Bookbinder | |
| 2006/0104968 | A1 | 5/2006 | Frost | |
| 2006/0247201 | A1 | 11/2006 | Frost | |
| 2007/0148156 | A1 | 6/2007 | Frost | |
| 2007/0275110 | A1 | 11/2007 | Dott et al. | 424/780 |
| 2008/0199452 | A1 | 8/2008 | Gaylis et al. | |

FOREIGN PATENT DOCUMENTS

| | | |
|---|---|---|
| WO | WO 99/03483 | 1/1999 |
| WO | WO 01/34176 A | 5/2001 |
| WO | WO2004/010934 A2 | 2/2004 |
| WO | WO2005/053733 A1 | 6/2005 |
| WO | WO 2006/005912 A2 * | 1/2006 |
| WO | WO 2006/138127 A | 12/2006 |
| WO | WO 2007/044809 | 4/2007 |
| WO | WO2008/030638 | 3/2008 |

OTHER PUBLICATIONS

Goodman et al., Dermatol Surg, 2003, vol. 29, p. 533-538.*
Best et al., An Evaluation of Solutions for Fragmentation and Dissolution of Gallstones and their Effect on Liver and Ductal Tissue, 1953, vol. 138, No. 4, p. 570-581.*
Löhr et al., Eur J Gastroenterol Hepatol., 1995, vol. 7, No. 2, p. 135-140.*
Brodyagin et al., "Effects of Hyaluronidase and Its Nonspecific Inhibitors (Heparin, Pipolphen, Ascorbic Acid) on Bile Secretion", 1971, p. 1025-1027.*
Martinez-Cuesta et al., Digestive Diseases and Science, 2003, vol. 48, No. 5, p. 898-905.*
Malmström et al., Critical Reviews in Oncology/Hematology, 2003, vol. 47, p. 109-126.*
Baumgartner G. Hyaluronidase in the Therapy of Malignant Diseases, Wien Klin Wochenschr Suppl. 1987;174:1-22 (Abstract only).
Giannantoni, Antonella; et al. Botulinum A Toxin Intravesical Injection in Patients With Painful Bladder Syndrome: 1-Year Followup, J Urol. Mar. 2008; vol. 179, pp. 1031-1034.
Maier U, et al. Metaphylactic Effect of Mitomycin C With and Without Hyaluronidase After Transurethral Resection of Bladder Cancer: Randomized Trial, J Urol. Mar. 1989;141(3):529-530(Abstract only).
U.S. Appl. No. 09/978,982, filed Oct. 15, 2001, Schmidt.
U.S. Appl. No. 10/194,805, filed Jul. 11, 2002, Donovan.
Baumgartner G. Hyaluronidase in the therapy of malignant diseases. Wien Klin Wochenschr Suppl. 1987: 174:1-22.
Bigalke H., et al., *Botulinum A Neurotoxin Inhibits Non-Cholinergic Synaptic Transmission in Mouse Spinal Cord Neurons in Culture*, Brain Research 360 (1985), pp. 318-324.
Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 31 (1981) 6; pp. 244-251.
Binz T. et al., The Complete Sequence of Botulinum Neurotoxin Type A and Comparison with Other Clostridial Neurotoxins, J Biological Chemistry 265(16), (1990), pp. 9153-9158.

(Continued)

*Primary Examiner* — Kade Ariani
(74) *Attorney, Agent, or Firm* — Ted A. Chan; Brigitte Phan; Debra Condino

(57) ABSTRACT

Disclosed herein are methods of using extracellular matrix digesting enzymes and neurotoxins, such as a *Clostridial* neurotoxins, to treat various medical conditions, such as overactive bladder, benign prostatic hyperplasia, hyperhidrosis, and cholecystitis for example.

15 Claims, No Drawings

OTHER PUBLICATIONS

Bushara K., *Botulinum toxin and rhinorrhea*, Otolaryngol Head Neck Surg. 114(3) (1996), 507.

Botulinum toxin type A in the treatment of focal, axillary and palmar hyperhidrosis and other hyperhidrotic conditions. European J. Neurology 6 (Supp 4) 1999, pp. S111-S115.

Carmen et al., SNAP-25a and -25b insoforms are both expressed in insulin-secreting cells and can function in insulin secretion. Biochem J 1;339 (pt 1) 1999, pp. 159-165.

Drugdex Evaluations, Hyaluronidas, publ. Thomson Healthcare, 1974-2008.

Dysport, SPC from the electronic Medicines Compendium, pp. 1-13.

Dykstra, Dennis D., et al., Treatment of Detrusor-Sphincter Dyssynergia with Botulinum A Toxin: A Double-Blind Study, Arch. Phys. Med. Rehabil. 1990, Jan. 71, pp. 24-26.

Fraser, Matthew Q., et al., *The Future of Bladder Control—Intravesical Drug Delivery, a Pinch of Pepper and Gene Therapy*, Reviews in Urology, vol. 4, No. 1, 2002, pp. 1-11.

Goodman G., Diffusion and short-term efficacy of botulinum toxin A after the addition of hyaluronidase and its possible application for the treatment of axillary hyperhidrosis, Dermatol Surg May 2003; 29(5), pp. 533-538.

Habermann E., et al., *Tetanus Toxin and Botulinum A and C Neurotoxins Inhibit Noradrenaline Release From Cultured Mouse Brain J Neurochem* 51(2) 1988, pp. 522-527.

Habermann E., *Inhibition by Tetanus and Botulinum A Toxin of the release of [3H] Noradrenaline and [3H]GABA From Rat Brain Homogenate*, Experientia 44 (1988), pp. 224-226.

Harrison's Principles of Internal Medicine (1998), edited by Anthony Fauci et al., 14th edition, and published by McGraw Hill.

Hylenex Recombinant, Mar. 2006, pamphlet insert, Baxter Heathcare Corp.

Jankovic J. et al., *Therapy With Botulinum Toxin*, Marcel Dekker, Inc., (1994), p. 5.

Katsambas A., et al., Cutaneous diseases of the foot: Unapproved treatments, Clin Dermatol Nov.-Dec. 2002, 20(6), pp. 689-699.

Kumar R and Seeberger LC., *Long-term safety, efficacy, and dosing of botulinum toxin type B (MYOBLOC®) in cervical dystonia (CD) and other movement disorders*, Mov Disord 2002; 17(Suppl 5), pp. S292-S293.

Li Y, et al., Sensory and motor denervation influences epidermal thickness in rat foot glabrous skin, Exp Neurol 1997; 147, pp. 452-462.

Massimo Lazzeri, Massimo Porena. The Challenge of the Overactive Bladder: From Laboratory to New Drugs. AEU-EBU Update Series 5 (2007) 250-258.

Maier U, Baumgartner G. Metaphylactic effect of mitomycin C with and without hyaluronidase after transurethral resection of bladder cancer: randomized trial. J Urol Mar. 1989; 141 (3): 529-30.

Mechanisms of the antinociceptive effect of subcutaneous BOTOX: inhibition of peripheral and central nociceptive processing. Cephalalgia Sep. 23(7) 2003, p. 649.

Micromedex Healthcare Series: Drugdex Drug Point Summary: Hyaluronidase, pp. 1-5.

Moyer E. et al., *Botulinum Toxin Type & Experimental and Clinical Experience*, being chapter 6, pp. 71-85 of "Therapy With Botulinum Toxin," edited by Jankovic, J. et al. (1994), Marcel Dekker, Inc. Neurology, 48 (1997), pp. 249-253.

Nitti Victor W., *Botulinum toxin for the treatment of idiopathic and neurogenic overactive bladder: State of the art*, Rev Urol 2006; 8(4):198-208.

Pearce, L. B., *Pharmacologic Characterization of Botulinum Toxin for Basic Science and Medicine*, Toxicon 35(9);1 373-1 412 at 1393, 1997.

Rogers J., et al., Injections of botulinum toxin A in foot dystonia, Neurology Apr. 1993;43 (4 Suppl 2).

Sanchez-Prieto, J., et al., *Botulinum Toxin A Blocks Glutamate Exocytosis From Guinea Pig Cerebral Cortical Synaptosomes*, Eur J. Biochem 165:1987; pp. 675-681.

Schantz, E.J., et al, *Properties and use of Botuilnum toxin and Other Microbial Neurotoxins in Medicine*, Microbiol Rev. 56:1992; pp. 80-99.

Sevim, S., et al., Botulinum toxin-A therapy for palmar and plantar hyperhidrosis, Acta Neurol Belg Dec. 2002;102(4):167-170.

Singh, *Critical Aspects of Bacteria/Protein Toxins*, pp. 63-84 (chapter 4) of Natural Toxins II, edited by B.R. Singh et al., Plenum Press, New York (1976).

Suputtitada, A., Local botulinum toxin type A injections in the treatment of spastic toes, Am J Phys Med Rehabil Oct. 2002; 81(10): pp. 770-775.

Tacks, L., et al., Idiopathic toe walking: Treatment with botulinum toxin A injection, Dev Med Child Neurol 2002; 44 (Suppl 91):6.

The Laryngoscope 109 (1999), pp. 1344-1346.

Van de Velde, H., et al., *Effects of different hyaluronidase concentrations and mechanical procedures for cumulus cell removal on the outcome of intracytoplasmic sperm injection*, Humar Reproduction, vol. 12, No. 10, 1997, pp. 2246-2250.

Victor W. Nitti, *Botulinum Toxin for the Treatment of Idiopathic and Neurogenic Overactive Bladder: State of the Art*, Reviews in Urology, 2006, vol. 8, No. 4, pp. 198-208.

Worthington Collagenase Sampling Program, Worthington Biochemical Corporation, 2008.

Chen, Danny; et al., "Effect of Dimethyl Sulfoxide on Bladder Tissue Penetration of Intravesical Paclitaxel". Clinical Cancer Research, vol. 9, 363-369, Jan. 2003, p. 363.

Maria G.; et al., "Relief by Botulinum Toxin of Voiding Dysfunction Due to Prostatitis" LANCET, Little, Browm and Co., Boston, US, vol. 352, No. 9128, Aug. 22, 1998, p. 625, XP002308256 ISSN: 0099-5355.

Smith, Christopher P.; et al., "Botulinum Toxin A inhibits Afferent Nerve Evoked Bladder Strip Contractions". J Urol Apr. 2002; 167(4 Suppl):4, p. 164.

Carl S; et al., *Treatment of interstitial cystitis with botulinum toxin A*, Eur Urol Suppl 2007;6(2):248 ABS-901 (Abstract Only).

Carl S; Laschke S, *Treatment of interstitial cystitis with botulinum toxin A*, J Urol 2007;177(4 Suppl):42 ABS-123 (Abstract Only).

Chancellor Michael B; Smith Christopher P, *A single surgeon's six-year experience with Botulinum toxin injection into the bladder and urethra*, J Urol Apr. 2004; 171(Suppl 4):138 ABS 517 (Abstract Only).

Chancellor Michael; Smith Christopher P, *One surgeon's experience in 50 patients with Botulinum toxin injection into the bladder and urethra*, J Urol Apr. 2002;167(4 Suppl):249-50 ABS-981 (Abstract Only).

Davies AM; et al., *Intravesical Botulinum a toxin (BOTOX™): Does it have a role in the management of interstitial cystitis?*, Eur Urol Suppl Apr. 2006;5(2):222 ABS-799 (Abstract Only).

De Miguel F; Chancellor MB, *Pittsburgh experience with Botulinum toxin A injection. Experiencia De Pittsburgh Con La Toxina Botulinica a Inyectable (SPA)*, Acta Urol Esp Mar. 2006;30(3):310-4 (Abstract Only).

Finamore PS; et al., *Assessing the effectiveness of BOTOX A injections as a treatment option for women with high tone pelvic floor muscle dysfunction*, Soc Urodyn Female Urol Meeting 2007;(Online):ABS-Poster 18 (Abstract Only).

Giannantoni A; et al., *Intravesical passive delivery of Botulinum A toxin in patients affected by painful bladder syndrome: A pilot study*, Eur Urol Suppl 2007;6(2):246 ABS-895 (Abstract Only).

Giannantoni A; et al., *Botulinum A toxin intravesical injections in the treatment of painful bladder syndrome: A pilot study + Comment*, Eur Urol Apr. 2006;49(4):704-9 (Abstract Only).

Giannantoni A; et al., *Botulinum A toxin intravesical injections in the treatment of bladder hypersensitive disorders: A pilot study*, Abstr Internat Continence Soc (ICS) 2005; ABS-264 (Abstract Only).

Giannantoni A; et al., *Botulinum A toxin intravesical injections in the treatment of painful bladder syndrome: A pilot study*, Eur Urol Suppl Apr. 2006;(5)2:118 Abs-383 (Abstract Only).

Giannantoni A; et al., Botulinum A Toxin Intravesical Injection in Patients With Painful Bladder Syndrome: 1-Year Followup, *J Urol* 2008; 179(3): 1031-1034. (Abstract Only).

Hampel C; et al., *Botulinum toxin detrusor injections in patients with non-neurogenic bladder hyperactivity*, Eur Urol Suppl Mar. 2005;4(3):61 ABS-236 (Abstract Only).

Kuo H-C; Liu H-T, *Intravesical Botulinum toxin A injections plus hydrodistension can reduce nerve growth factor production and control bladder pain in interstitial cystitis*, Urology 2007;70(3):463-468 (Abstract Only).

Kuo H-C; Liu H-T, *Intravesical Botulinum toxin A injections reduced nerve growth factor production and bladder pain in chronic interstitial cystitis*, J Urol 2007;177(4 Suppl):42 ABS-122 (Abstract Only).

Kuo Hann-Chorng, *Preliminary results of suburothelial injection of Botulinum A toxin in the treatment of chronic interstitial cystitis*, Urol Int 2005;75(2):170-4 (Abstract Only).

Loch A; et al., *Botulinum-A Toxin detrusor injections in the treatment of non-neurologic and neurologic cases of urge incontinence*, J Urol Apr. 2003;169(Supp 4):124 ABS 481 (Abstract Only).

Loch A; et al., *Botulinum-A toxin detrusor injections in the treatment of non-neurologic and neurologic cases of urge incontinence*, Eur Urol Feb. 2003;2(Suppl 1):172 ABS 678 (Abstract Only).

Mustafa AW; et al., *A quantitative [quantitative] assessment of the effect of Botulinum toxin type A on voiding detrusor contractility*, BJU Int Jun. 2005;95(5 Suppl):11 ABS-59 (Abstract Only).

Ramsay A; et al., *Intravesical Botulinum toxin type A in chronic interstitial cystitis: Results of a pilot study*, Surgeon 2007;5(6):331-3 (Abstract Only).

Ramsay A; et al., *Intravesical Botulinum toxin type A in interstitial cystitis*, Eur Urol Suppl 2007;6(2):248 ABS-902 (Abstract Only).

Schumacher S; et al., *Therapy of neurogenic and non neurogenic detrusor overactivity with detrusor-injections of botulinum-A toxin and continent vesicostomy*, Eur Urol Feb. 2003;2(Suppl 1):141 ABS 554 (Abstract Only).

Smith Christopher P; et al., *Botulinum toxin A has antinociceptive effects in treating interstitial cystitis + Comment*, Urology Nov. 2004; 64(5):871-5 (Abstract Only).

Smith Christopher P; et al., *Single-institution experience in 110 patients with Botulinum toxin A injection into bladder or urethra*, Urology Jan. 2005;65(1):37-41 (Abstract Only).

Sweeney D; et al., *Intravesical instillation of Botulinum toxin A for overactive bladder*, Abstr Internat Continence Soc (ICS) 2005; ABS-565 (Abstract Only).

Taha M; et al., *A randomized controlled trial of bacillus Calmette-Guerin and Botulinum toxin-A for the treatment of refractory interstitial [interstitial] cystitis*, Neurourol Urodyn 2007;26(5):735 ABS-MA107 (Abstract Only).

Thomson Angus JM; et al., *The use of Botulinum toxin type A (BOTOX®) as treatment for intractable chronic pelvic pain associated with spasm of the levator ani muscles*, BJOG Feb. 2005; 112(2): 247-9 (Abstract Only).

Wein Alan J; et al., *Single-institution experience in 110 pantients with Botulinum toxin A injection into bladder or urethra + Commentary*, J Urol Aug. 2005;174(2):611-2 (Abstract Only).

\* cited by examiner

BOTULINUM TOXIN COMPOSITIONS AND METHODS

CROSS-REFERENCE

This application claims the benefit of U.S. Provisional Application No. 60/890,052, filed Feb. 15, 2007, the contents of which are hereby incorporated by reference in their entirety.

BACKGROUND

The present invention relates to the use of extracellular matrix digesting enzymes and neurotoxins to treat various medical conditions/disorders, such as overactive bladder, urinary incontinence due to overactive bladder or unstable detrusor sphincter, benign prostatic hyperplasia and associated bladder voiding complications, urinary retention that is secondary to having a spastic sphincter or a hypertrophied bladder neck, neurogenic bladder dysfunction (e.g. secondary to for example, Parkinson's disease, spinal cord injury, stroke or multiple sclerosis), hyperhidrosis and gall bladder inflammation (cholecystitis).

Neurotoxins, and in particular botulinum toxins, are increasingly finding useful application in treating various medical conditions. Such treatments are typically focally delivered via injections that penetrate the skin or organ lining. This can lead to difficulty in delivering the treatment due to complications from needle penetration, patient concerns such as needle phobia, pain and physician application in the treatment of several urological conditions including overactive bladder (OAB) and detrusor hyperreflexia (DH) which cause bothersome symptoms such as voiding urgency, excessive voiding frequency and incontinence, for example. A detailed discussion of the use and techniques for utilizing botulinum toxin to treat overactive bladder can be found in "Botulinum toxin for the treatment of idiopathic and neurogenic overactive bladder: State of the art" Nitti Victor W. Rev Urol 2006; 8(4):198-208. As detailed therein, botulinum toxin is injected into the bladder wall and the number of injections (between 15 to 50 injections of 100 to 1000 units of botulinum toxin type A and 10 injections of 5000 units botulinum toxin type B) depends on the well known effect and potency difference between the serotype of botulinum toxin utilized, as well as the amount of total toxin and dilution of toxin utilized, as detailed in therein and known in the art.

Incontinence, one symptom of various urologic disorders, includes urge incontinence and stress incontinence. Urge incontinence involves a strong, sudden need to urinate, followed by inappropriate bladder contraction, which then results in leakage. What is troublesome is that it is often the case that these contractions occur regardless of the amount of urine that is in a sufferer's bladder, that is, the bladder does not necessarily have to be so full and under pressure from urine contained therein to result undesirable leakage. Urge incontinence can be a result of neurological injuries (such as spinal cord injury or stroke), neurological diseases (such as multiple sclerosis), infection, bladder cancer, bladder stones, bladder inflammation, or bladder outlet obstruction, for example. While these conditions can be found both in men and women, men have an additional burden in that urge incontinence may also be due to neurologic disease or bladder changes caused by benign prostatic hypertrophy (BPH) or bladder outlet obstruction from an enlarged prostate, for example.

Stress incontinence is an involuntary loss of urine that occurs during physical activity, such as coughing, sneezing, laughing, or exercise. A person can suffer from one or both types of incontinence, and when suffering from both, it is called mixed incontinence. Despite all of the knowledge associated with incontinence, the majority of cases of urge incontinence are idiopathic, which means a specific cause cannot be identified. Urge incontinence may occur in anyone at any age, and it is more common in women and the elderly.

The detrusor of the bladder is the muscle that expels urine from the bladder. Consequences of detrusor hyperreflexia include poor bladder compliance, high intravesical pressure, and reduction in bladder capacity, all of which may result in deterioration of the upper urinary tract.

It is thought that botulinum toxin exerts its effect on bladder hyperactivity by paralyzing the detrusor muscle in the bladder wall or possibly impacting afferent pathways in the bladder and reducing sensory receptors in suburothelial nerves. These effects possibly account for the improvement in urinary incontinence, bladder capacity and reduction in bladder detrusor pressures that are seen when the bladder walls are injected with botulinum toxins. Examples of botulinum toxin use to treat various urologic disorders can be found in "Botulinum Toxin Treatment of Spastic Bladder", by Dott, C. et al., U.S. Patent App. Publication No. US 2007/0275110A1 and "Methods for the use of neurotoxin in the treatment of urologic disorders", by Doshi, R., U.S. Patent App. Publication No. 2004/0067235A1, both herein incorporated by reference. Other known potential urological applications for neurotoxins include the treatment of a variety of disorders of the prostate including benign prostatic hyperplasia (BPH), prostatitis, and prostate cancer (see, e.g., U.S. Pat. No. 6,365,164, herein incorporated by reference in its entirety.)

To date, botulinum toxin has shown promising early results for treatment of lower urinary tract symptoms including obstructive and irritative voiding symptoms attributed to BPH. Both subjective (symptoms) and objective (flow rates) improvements have been observed. The prostate is a partially glandular and partially fibromuscular gland of the male reproductive system. During aging, the prostate tends to enlarge (hypertrophy). This prostatic enlargement can lead to urethral obstruction and voiding dysfunction. This is because the urethra passes through the prostate (prostatic urethra) as it leads to the external urethral orifice. A detailed discussion of prostate anatomy (including lobes, stroma, nerve fiber types and innervation) can be found in published U.S. patent application Ser. No. 09/978,982, filed Oct. 15, 2001, and entitled "Use of neurotoxin therapy for treatment of urologic and related disorders", U.S. Published Patent Application No. 20020025327 A1, herein incorporated by reference in its entirety, in addition to standard anatomy texts.

Botulinum toxin is thought to affect nerve terminals in the prostate and the release of neurotransmitters including acetyicholine, sensory neuropeptides, and noradrenalin. These effects may alter neural control within the prostate. Preliminary reports suggest that botulinum toxin may also have a role in the management of prostate cancer, possibly by inhibiting inflammation and the down regulation of COX-2 expression.

In humans, the gall bladder is the organ that stores about 50 ml of bile (yellow or green alkaline fluid secreted by hepatocytes from the liver of most vertebrates) until needed for digestion. Bile is discharged into the duodenum where it aids the process of digestion of lipids. The gallbladder is about 100 to 120 mm long in humans and is connected to the liver and the duodenum by the biliary tract. A cystic duct connects the gallbladder to the common hepatic duct to form the common bile duct, which then joins the pancreatic duct, and enters through the hepatopancreatic ampulla at the major duodenal papilla. The fundus of the gallbladder is the part farthest from the duct, located by the lower border of the liver at the same level as the transpyloric plane.

Unfortunately, inflammation of the gall bladder, called cholecystitis, can occur and is typically caused by the presence of gall stones (choleliths, crystalline bodies formed by accretion or concretion of normal or abnormal bile components in the gallbladder) which commonly block the cystic duct directly leading to a thickening of the bile, bile stasis, and even secondary infection by gut organisms, predominantly *E coli* species. This results in inflammation of the wall of the gallbladder. The gallbladder can also become inflamed and infected in the absence of galls stones. This is known as acute acalculous cholecystitis. Chronic, low-level inflammation can lead to a chronic cholecystitis, where the gallbladder is fibrotic and calcified.

In order to gain access and visualize the gall bladder and ducts, endoscopic retrograde cholangiopancreatography (ERCP) can be utilized, a technique that combines the use of endoscopy and fluoroscopy to diagnose and treat problems of the biliary systems. Aided by a video endoscope, ERCP can utilize x-ray examination to investigate and access bile ducts. The inside of the stomach and duodenum can be seen through the endoscope, and dyes are commonly injected by medical personnel into the ducts in the biliary tree so they can be seen on x-rays. ERCP is used primarily to diagnose and treat conditions of the bile ducts, including investigation of and removal gallstones, inflammatory strictures (scars), leaks (from trauma and surgery), and cancer. ERCP combines the use of x-rays and endoscopy and is performed for diagnostic or therapeutic reasons. In some instances, a second camera can be inserted through the channel of the first endoscope (this technique is termed duodenoscope-assisted cholangiopancreatoscopy (DACP) or mother-daughter ERCP). The daughter scope can be used to administer direct electrohydraulic lithotripsy to break up stones, or to help in diagnosis by directly visualizing the duct (as opposed to obtaining X-ray images).

The large size of the botulinum toxin molecule can limit its ability to diffuse, and thus prohibits it from reaching both afferent and efferent nerve fibers. As a result, current methods of administration for OAB, for example, require many injections (typically 20 to 50) of botulinum toxin into the bladder muscle wall or into the prostate. Other examples of botulinum toxin uses includes the treatment of chronic migraine with botulinum toxin, which requires approximately 30 injections into the head and neck musculature, and axillary hyperhidrosis, which requires numerous injections to the dermal skin layer in the axilla (typically anywhere from 10 to 40 injections per axilla, depending on the severity of the condition, area overproducing sweat, size of the patient and concentration, amount and type of botulinum toxin used).

The genus *Clostridium* has more than one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

About 50 picograms of a commercially available botulinum toxin type A (a purified neurotoxin complex available from Allergan, Inc., of Irvine, Calif. under the trade name BOTOX® in 100 unit vials) is a $LD_{50}$ in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 1 2 million times more lethal than cholera. Singh, *Critical Aspects of Bacteria/Protein Toxins*, pages 63-84 (chapter 4) of Natural Toxins II, edited by B. R. Singh et al., Plenum Press, New York (1976) (where the stated $LD_{50}$ of botulinum toxin type A of 0.3 ng equals 1 unit is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

Seven immunologically distinct botulinum neurotoxins have been characterized, these being respectively botulinum neurotoxin serotypes A, B, $C_1$, D, E, F and G, each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Moyer E et al., *Botulinum Toxin Type 8: Experimental and Clinical Experience*, being chapter 6, pages 71-85 of "Therapy With Botulinum Toxin", edited by Jankovic, J. et al. (1994), Marcel Dekker, Inc. Botulinum toxin apparently binds with high affinity to cholinergic motor neurons, is translocated into the neuron, and blocks the release of acetylcholine. Additional uptake can take place through low affinity receptors, as well as by phagocytosis and pinocytosis.

Regardless of stereotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface. In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc ($Zn^{2+}$) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G, cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype $C_1$ was originally thought to cleave syntaxin, but was found to cleave syntaxin and SNAP-25. Each of the botulinum toxins specifically cleaves a different bond, except botulinum toxin type B (and tetanus toxin) which cleave the same bond. Each of these cleavages block the process of vesicle-membrane docking, thereby preventing exocytosis of vesicle content.

Botulinum toxins have been used in clinical settings for the treatment of neuromuscular disorders characterized by hyperactive skeletal muscles (i.e. motor disorders). Almost twenty years ago, in 1989, a botulinum toxin type A complex was approved by the U.S. Food and Drug Administration for the treatment of blepharospasm, strabismus and hemifacial spasm. Subsequently, a botulinum toxin type A was also approved by the FDA for the treatment of cervical dystonia and for the treatment of glabellar lines, and a botulinum toxin type B was approved for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months, although significantly longer periods of therapeutic activity have been reported.

Although all the botulinum toxin serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. *Biochem J* 1;339 (pt 1):159-65.1999, and *MovDisord,* 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by *Clostridial bacterium* as complexes comprising the 150 kD botulinum toxin protein molecule along with associated non-toxin proteins. Thus, the botulinum toxin type A complex can be produced by *Clostridial bacterium* as 900 kD, 500 kD and 300 kD forms. Botulinum toxin types B and $C_1$ are apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule, and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain J* Neurochem 51(2); 522-527:1988)), CGRP, substance P, and glutamate (Sanchez-Prieto, J., et al., *Botulinum Toxin A Blocks Glutamate Exocytosis From Guinea Pig Cerebral Cortical Synaptosomes,* Eur J. Biochem 165; 675-681:1897). Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine,* Toxicon 35(9);1 373-1 412 at 1393; Bigalke H., et al., *Botulinum A Neurotoxin Inhibits Non-Cholinergic Synaptic Transmission in Mouse Spinal Cord Neurons in Culture,* Brain Research 360;318-324:1985; Habermann E., *Inhibition by Tetanus and Botulinum A Toxin of the release of [3H] Noradrenaline and [3H] GABA From Rat Brain Homogenate,* Experientia 44;224-226: 1988, Bigalke H., et al., *Tetanus Toxin and Botulinum A Toxin Inhibit Release and Uptake of Various Transmitters, as Studied with Particulate Preparations From Rat Brain and Spinal Cord,* Naunyn-Schmiedeberg's Arch Pharmacol 31 6;244-251 :1 981, and; Jankovic J. et al., *Therapy With Botulinum Toxin,* Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype, only cleave a portion of the toxin produced. The exact proportion of nicked to unnicked molecules depends on the length of incubation and the temperature of the culture. Therefore, a certain percentage of any preparation of, for example, the botulinum toxin type B toxin, is likely to be inactive, possibly accounting for the known significantly lower potency of botulinum toxin type B, as compared to botulinum toxin type A (and thus the routine use of many thousands of units of botulinum toxin type B, as known in the art, see e.g. "*Long-term safety, efficacy, and dosing of botulinum toxin type B (MYOBLOC®) in cervical dystonia (CD) and other movement disorders*" Kumar R and Seeberger L C. Mov Disord 2002; 17(Suppl 5):S292-S293). The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of *Clostridium botulinum* with characteristics of $\geq 3 \times 10^7$ U/mg, an $A_{260}/A_{278}$ of less than 0.60 and a distinct pattern of banding on gel electrophoresis. The known Schantz process can be used to obtain crystalline botulinum toxin type A, as set forth in Schantz, E. J., et al, *Properties and use of Botuilnum toxin and Other Microbial Neurotoxins in Medicine,* Microbiol Rev. 56;80-99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1\text{-}2\times10^8$ $LD_{50}$ U/mg or greater; purified botulinum toxin type B with an approximately 156 kD molecular weight with a specific potency of $1\text{-}2\times10^8$ $LD_{50}$ U/mg or greater; and purified botulinum toxin type F with an approximately 155 kD molecular weight with a specific potency of $1\text{-}2\times10^7$ $LD_{50}$ U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure botulinum toxin can also be used to prepare a pharmaceutical composition for use in accordance with the present disclosure.

As with enzymes generally, the biological activities of botulinum toxins (which are intracellular peptidases) is dependant, at least in part, upon their 3-dimensional conformation. Thus, botulinum toxin type A is detoxified by heat, various chemicals, surface stretching, and surface drying. Additionally, it is known that dilution of the toxin complex obtained by the known culturing, fermentation and purification to the much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can be stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. Botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 U of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks (*Neurology*, 48:249-53, 1997). It has been reported that botulinum toxin type A has been used in clinical settings as follows:

(1) about 75-125 U of BOTOX® per intramuscular injection (multiple muscles) to treat cervical dystonia;

(2) 5-10 U of BOTOX® per intramuscular injection to treat glabellar lines (brow furrows) (5 units injected intramuscularly into the procerus muscle and 10 units injected intramuscularly into each corrugator supercilii muscle);

(3) about 30-80 U of BOTOX® to treat constipation by intrasphincter injection of the puborectalis muscle;

(4) about 1-5 U per muscle of intramuscularly injected BOTOX® to treat blepharospasm by injecting the lateral pre-tarsal orbicularis oculi muscle of the upper lid and the lateral pre-tarsal orbicularis oculi of the lower lid;

(5) to treat strabismus, extraocular muscles have been injected intramuscularly with between about 1-5 U of BOTOX®, the amount injected varying based upon both the size of the muscle to be injected and the extent of muscle paralysis desired (i.e. amount of diopter correction desired);

(6) to treat upper limb spasticity following stroke by intramuscular injections of BOTOX® into five different upper limb flexor muscles, as follows:
(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session;

(7) to treat migraine, pericranial (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that botulinum toxin type A can have an efficacy for up to 12 months (*European J. Neurology* 6 (Supp 4): S111-S1150: 1999), and in some circumstances for as long as 27 months, when used to treat glands, such as in the treatment of hype rhydrosis. See e.g. Bushara K., *Botulinum toxin and rhinorrhea*, Otolaryngol Head Neck Surg 1996; 114(3):507, and *The Laryngoscope* 109:1344-1346:1999. However, the usual duration of effect of an intramuscular injection of BOTOX® is typically about 3 to 4 months.

The success of botulinum toxin type A to treat a variety of clinical conditions has led to interest in other botulinum toxin serotypes. Two commercially available botulinum type A preparations for use in humans are BOTOX® available from Allergan, Inc., of Irvine, Calif., and DYSPORT® available from Beaufour Ipsen, Porton Down, England. A botulinum toxin type B preparation (MYOBLOC®) is available from Elan Pharmaceuticals of San Francisco, Calif.

A botulinum toxin has also been proposed for or has been used to treat otitis media of the ear (U.S. Pat. No. 5,766,605), inner ear disorders (U.S. Pat. Nos. 6,265,379; 6,358,926), tension headache, (U.S. Pat. No. 6,458,365), migraine headache pain (U.S. Pat. No. 5,714,468), post-operative pain and visceral pain (U.S. Pat. No. 6,464,986), hair growth and hair retention (U.S. Pat. No. 6,299,893), psoriasis and dermatitis (U.S. Pat. No. 5,670,484), injured muscles (U.S. Pat. No. 6,423,319) various cancers (U.S. Pat. No. 6,139,845), smooth muscle disorders (U.S. Pat. No. 5,437,291), and neurogenic inflammation (U.S. Pat. No. 6,063,768). Controlled release toxin implants are known (see e.g. U.S. Pat. Nos. 6,306,423 and 6,312,708) as is transdermal botulinum toxin administration (U.S. patent application Ser. No. 10/194805).

Additionally, a botulinum toxin may have an effect to reduce induced inflammatory pain in a rat formalin model. Aoki K., et al, Mechanisms of the antinociceptive effect of subcutaneous BOTOX®: Inhibition of peripheral and central nociceptive processing, Cephalalgia September 2003;23(7): 649. Furthermore, it has been reported that botulinum toxin nerve blockage can cause a reduction of epidermal thickness. Li Y, et al., Sensory and motor denervation influences epidermal thickness in rat foot glabrous skin, Exp Neurol 1997; 147:452-462 (see page 459). Finally, it is known to administer a botulinum toxin to the foot to treat excessive foot sweating (Katsambas A., et al., Cutaneous diseases of the foot: Unapproved treatments, Clin Dermatol November-December 2002;20(6):689-699; Sevim, S., et al., Botulinum toxin-A therapy for palmar and plantar hyperhidrosis, Acta Neurol Belg December 2002;102(4):167-70), spastic toes (Suputtitada, A., Local botulinum toxin type A injections in the treatment of spastic toes, Am J Phys Med Rehabil October 2002; 81(10):770-5), idiopathic toe walking (Tacks, L., et al., Idiopathic toe walking: Treatment with botulinum toxin A injection, Dev Med Child Neurol 2002;44(Suppl 91):6), and foot dystonia (Rogers J., et al., Injections of botulinum toxin A in foot dystonia, Neurology April 1993;43(4 Suppl 2)). Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively).

Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Additionally, both the tetanus toxin and the botulinum toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of botulinum toxin by peripheral cholinergic neurons results in little if any retrograde transport, inhibition of acetylcholine exocytosis from the intoxicated peripheral motor neurons and a flaccid paralysis.

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains. Binz T. et al., The Complete Sequence of Botulinum Neurotoxin Type A and Comparison with Other Clostridial Neurotoxins, J Biological Chemistry 265(16); 9153-9158: 1990.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A variety of substances, termed proteolytic enzymes, degrade or digest substances found in the extracellular matrix. These include the family of hyaluronidases, plasminogen activators and collagenase, for example. Hyaluronidase causes hydrolysis of hyaluronic acid, a polysaccharide (nonsulfated glycosaminoglycan) found in the intercellular matrix of connective tissue. Hyaluronidase temporarily reduces the viscosity of the extracellular matrix (tissue cement) by digesting hyaluronic acid or hyaluronate, which is widely distributed throughout connective, epithelial, and neural tissues. This effect promotes the diffusion or spread of other drugs like anesthetic agents. Hyaluronidase may be injected into connective tissue to enhance the effects of co-injected drugs.

Hyaluroronidase can be obtained from a variety of sources and is typically derived from testicular tissue extracts. For example, ISTA Pharmaceuticals of Irvine, Calif., USA manufactures and distributes VITRASE (a sheep sourced (ovine) form of hyaluronidase), which is just one example of a hyaluronidase for injection. VITRASE is an injectable drug approved by the U.S. FDA as an adjunct to (in combination with) other injected drugs to increase their absorption and dispersion. As stated previously, hyaluronidase has been used most commonly in combination with local anesthetics in the setting of ophthalmic (eye) surgery. Hyaluronidase increases tissue permeability and promotes the spread or dispersion of other drugs, for example, speeding the onset of action for an anesthetic. VITRASE is also approved for use as an adjunct to rehydrating agents, and for use with certain imaging agents. Hyaluronidase is also available as a recombinant purified preparation of the enzyme recombinant human hyaluronidase, an example of which is HYLENEX, which is marketed by Baxter Healthcare Corporation, Deerfield, Ill., USA. HYLENEX (a recombinant hyaluronidase) is available as a sterile clear, colorless, nonpreserved ready for use solution (each mL containing 150 USP units of recombinant human hyaluronidase with 8.f mg sodium chloride, 1.4 mg bibasic sodium phosphate, 1.0 mg human albumin, 0.9 mg edetate, 0.3 mg calcium chloride, and sodium hydroxide for pH adjustment. Another exemplary hyaluronidase produced from sheep testes is named HYALASE, by Aventis Pharma, Lane Cove, NSW, Australia.

Hyaluronidase increases dispersion in the interstitial matrix provided local pressure is adequate to furnish the necessary mechanical impulse. Such an impulse is normally initiated by injected solutions and the rate of diffusion is proportionate to the amount of enzyme. The extent of diffusion is also proportionate to the volume of solution, as known in the art.

Investigation of maintenance of efficacy, spread of effect and decrease in required dose of botulinum toxin administered along with hyaluronidase for treating axillary hyperhidrosis has been reported ("Diffusion and short-term efficacy of botulinum toxin A after the addition of hyaluronidase and its possible application for the treatment of axillary hyperhidrosis" by Goodman G. *Dermatol Surg* May 2003; 29(5):533-8. Here a formulation/mixture containing a botulinum toxin and a hyaluronidase is injected to treat hyperhidrosis, as well as administration of botulinum toxin and superadded hyaluronidase.

Other proteolytic enzymes include collagenase and plasminogen activators which digest extracellular matrix proteins. Plasminogen activators (PA) belong to a class of serine proteases that have considerable substrate specificity and convert the inactive zymogen plasminogen to plasmin. Plasmin is a general protease which is capable of degrading many proteins including laminin, fibronectin and activating latent collagenase moieties.

What is needed therefore is a method for treating various disorders that reduces the amount of botulinum toxin administered to a patient. More particularly a method is needed that reduces, or more preferably even eliminates, the number of, or need for, injection of neurotoxins, such as botulinum toxins, to treat various disorders.

SUMMARY

The present disclosure meets the need for a method by which cholinerically-influenced disorders can be treated by reducing or even eliminating the number of, and even the need for, injections endured by a patient in order to treat the disorder that the patient suffers from.

Definitions

As used herein, the words or terms set forth below have the following definitions.

"About" means that the item, parameter or term so qualified encompasses a range of plus or minus ten percent above and below the value of the stated item, parameter or term.

"Target" or "target area" means that location/area or tissue or gland of a patient's anatomy in which the desired effect of the administered neurotoxin is exerted. A target can include, but is not limited to a muscle, such as a detrusor muscle of a bladder, or neurons that innervate a gland or muscle that is overactive, such as the neurons that control sweat production of sweat glands in the dermis of patient having hyperhidrosis, or contraction of a targeted muscle, such a detrusor muscle and/or a urethral sphincter, for example. Typically, the target is within 5 inches of the locale of the administration of a composition of the instant invention, preferably within 3 inches and even more preferably within 1 inch.

"Administration", "administering" or "to administer" means the step of giving (i.e. administering) a composition to a subject, such as a pharmaceutical composition. The pharmaceutical compositions disclosed herein are "locally administered" by e.g. intramuscular (i.m.), intradermal, subcutaneous administration, intraperitoneal (i.p.) administration, topical (transdermal), instillation (e.g. intravesicular instillation) and implantation (e.g. a slow-release device such as polymeric implant) routes of administration.

"Botulinum toxin" means a neurotoxin produced by *Clostridium botulinum*, as well as a botulinum toxin (or the light chain or the heavy chain thereof) made recombinantly by a non-Clostridial species. The phrase "botulinum toxin", as used herein, encompasses the botulinum toxin serotypes A, B, $C_1$, D, E, F and G. Botulinum toxin, as used herein, also encompasses both a botulinum toxin complex (i.e. the 300, 600 and 900 kDa complexes) as well as the purified botulinum toxin (i.e. about 150 kDa). "Purified botulinum toxin" is defined as a botulinum toxin that is isolated, or substantially isolated, from other proteins, including proteins that form a botulinum toxin complex. A purified botulinum toxin may be greater than 95% pure, and preferably is greater than 99% pure. The botulinum $C_2$ and $C_3$ cytotoxins, not being neurotoxins, are excluded from the scope of the present invention.

"Clostridial neurotoxin" means a neurotoxin produced from, or native to, a Clostridial bacterium, such as *Clostridium botulinum, Clostridium butyricum* or *Clostridium beratti,* as well as a Clostridial neurotoxin made recombinantly by a non-Clostridial species.

"Modified botulinum toxin" means a botulinum toxin that has had at least one of its amino acids deleted, modified, or replaced, as compared to a native botulinum toxin. Additionally, the modified botulinum toxin can be a recombinantly produced neurotoxin, or a derivative or fragment of a recombinantly made neurotoxin. A modified botulinum toxin retains at least one biological activity of the native botulinum toxin, such as, the ability to bind to a botulinum toxin receptor, or the ability to inhibit neurotransmitter release from a neuron. One example of a modified botulinum toxin is a botulinum toxin that has a light chain from one botulinum toxin serotype (such as serotype A), and a heavy chain from a different botulinum toxin serotype (such as serotype B). Another example of a modified botulinum toxin is a botulinum toxin coupled to a neurotransmitter, such as substance P.

A "therapeutically effective" amount of the neurotoxin is the dosage sufficient to inhibit neuronal activity for at least one week, more preferably one month, most preferably for approximately 6 to 9 months or longer and up to 5 years. Dosing can be single dosage or cumulative (serial dosing), and can be readily determined by one skilled in the art. Neurotoxin, such a botulinum toxin, can be delivered serially (i.e., one time per month, one time per every six months) such that an optimal amount of toxin is administered in accordance with the severity of the disorder treated and beneficial results are maintained. Such a dosage schedule is readily determined by one skilled in the art based on, e.g., patient size, the neurotoxin selected, the condition to be treated, severity of the disorder and other variables known in the art.

"Patient" means a human or non-human subject receiving medical or veterinary care. Accordingly, as disclosed herein, the compositions may be used in treating any animal, such as mammals.

"Sufficient amount" means that amount of a substance, composition of element of a composition that is enough to meet the needs under the situation or a proposed end. For example, in treating a particular disorder, it is that amount of botulinum toxin that results in a desired outcome, e.g. a decrease in detrusor muscle spasm or decrease in excessive sweat production.

"Cholinergically-influenced disorder" is a disorder that results from the dysfunction of a gland, organ or tissue that is the result of over or under activity of the gland, organ or tissue, or abnormal/disruptive enlargement of the gland organ or tissue, wherein the gland organ of tissue is influenced/innervated by acetylcholine releasing neurons. Non-limiting examples of cholinergically-influenced disorders include, hyperhidrosis, overactive bladder, and benign prostatic hyperplasia, for example. The term "urologic disorder" includes, but is not limited to, overactive bladder, detrusor hyperreflexia, detrusor instability, neurogenic bladder, idiopathic bladder, benign prostate hyperplasia and urinary incontinence.

An extracellular matrix digesting enzyme is an enzyme that digests/breaks down at least one component of the extracellular matrix. Exemplary extracellular matrix digesting enzymes include hyaluronidase, which digests hyaluronic acid and has potential application in both the bladder and prostate for disorders such as overactive bladder, neurogenic bladder, benign prostatic hyperplasia, prostitis, and prostate cancer. Other enzymes which digest the extracelluar matrix including collagenase and plasminogen activators such as tissue plasminogen activator and urokinase which may have similar application by digesting the extracellular matrix to thereby enhancing diffusion of neurotoxins, and reduce the number of or eliminate the need for injection of neurotoxin, in accordance with one aspect of the present teachings.

A surface area is simply a particular area of a subject/patient, such as a skin surface or internal surface, to which compositions of the instant disclosure are administered. Non-limiting examples of a surface area include an axillary skin surface area, a palmar skin surface area, a gall bladder surface area and a plantar skin surface area.

A "luminal surface area" of a patient/subject is an area that faces a lumen, as well known in the art. Non-limiting examples include a bladder luminal surface area, nasal luminal surface area, a prostate luminal surface area, an esophageal luminal surface area, stomach luminal surface area, gall bladder luminal surface area, intestinal luminal surface area and a vascular luminal surface area, for example.

"Intravesically administered" or "intravesical administration" means instillation of a composition into a lumen to contact a luminal surface area, such as a bladder luminal surface area, for example, by any known suitable and appropriate means. Intravesical administration excludes, however, injection into a wall facing the lumen, such as a bladder wall.

"Alleviating" means a reduction in the occurrence of a symptom that is associated with a cholinergically-influenced disorder. For example, alleviating includes some reduction, significant reduction, near total reduction, and total reduction of at lease one symptom associated with hyperhidrosis, overactive bladder, and benign prostate hyperplasia, for example, or any disorder treated in accordance with the methods disclosed herein. An exemplary symptom of hyperhidrosis is excessive sweating, for overactive bladder and benign prostate hyperplasia, exemplary symptoms can be incontinence or retention, for example. An alleviating effect may not appear clinically for between 1 to 7 days after administration of a Clostridial toxin, such as a botulinum toxin, to a patient.

"Treating" means to alleviate (or to eliminate) at least one symptom of a cholinergically-influenced disorder, either temporarily or permanently.

A method for treating a patient having a cholinergically-influenced disorder, in accordance with the present disclosure, can comprise the steps of administering a first composition containing an extracellular matrix digesting enzyme to a surface area of the patient, followed by allowing a sufficient amount of time to pass for the extracellular matrix digesting enzyme to diffuse through the surface area, then administering a second composition containing a botulinum toxin to the surface area, and subsequently allowing sufficient time for the botulinum toxin to diffuse through the surface area to thereby alleviate at least one symptom associated with the cholinergically-influenced disorder and treat the patient having the cholinergically-influenced disorder. In particular instances, the surface area is a luminal surface area such as bladder luminal surface area. The extracellular matrix digesting enzyme is a hyaluronidase, tissue plasminogen activator and collagenase, for example, while the botulinum toxin is selected from the group consisting of botulinum toxin type A, B, C, D, E, F, and G.

Various methods of administration can be utilized for administration of the compositions useful in practicing the methods disclosed herein. In one instance, administration of the extracellular matrix digesting enzyme and botulinum toxin to a bladder luminal surface area is achieved by instillation of a composition containing an extracellular matrix digesting enzyme, as well as instillation of a composition containing botulinum toxin, into a bladder, for example.

Additionally, due to the synergistic effects provided by methods practiced in accordance with the teachings disclosed herein, administration of the extracellular matrix digesting enzyme can be accomplished by injection, for example into a bladder wall, or subdermally injected to a skin surface area (such as into an armpit (axilla), palmer or plantar surface, for example), while administration of a neurotoxin containing second composition is accomplished by instillation into the bladder, or sprayed, swabbed or smeared onto the skin surface area, respectively, thereby avoiding any need for injection of the botulinum toxin. Conversely, it is also contemplated that administration of the extracellular matrix digesting enzyme (a first composition) can be accomplished by instillation of the first composition into a bladder or sprayed, swabbed or smeared onto the skin surface area, and administration of the botulinum toxin is accomplished by injection of the second composition (containing a neurotoxin, such as a botulinum toxin) into a bladder wall or subdermally into the skin surface area, respectively.

Accordingly, administration of the botulinum toxin can be achieved by less than 20 injections into the bladder wall, more preferably by less than 10 injections into the bladder wall and most preferably by performing between 1 and 5 injections into the bladder wall. For example, a total of 5 injections of neurotoxin, such as botulinum toxin, after administration of the first composition having the extracellular matrix digesting enzyme, can be administered as follows: 1 injection to the dome of a bladder, 1 injection to an ventral wall of the bladder wall, 1 injection to a dorsal wall of the bladder, and 1 injection each into each lateral wall (left and right lateral wall of the bladder) for a total of five injections. Particularly useful botulinum toxin include botulinum toxin selected from the group consisting of botulinum toxin types A, B, $C_1$, D, E, F and G.

In particular embodiments, the methods disclosed herein can include further steps of emptying the bladder prior to administration of a composition containing an extracellular matrix digesting enzyme and optionally emptying the bladder after administration of the composition containing the extracellular matrix digesting enzyme, and optionally emptying the bladder after administration of the second composition that contains a neurotoxin, such as a botulinum toxin. As stated above, the methods disclosed herein can include removing the first composition (containing at least one extracellular matrix digesting enzyme) and removing the second composition (containing at least one neurotoxin, such as a botulinum toxin).

Exemplary cholinergically-influenced disorders that can be treated in accordance with the instant disclosure include a urologic disorder such as a bladder disorder or a prostate disorder. Exemplary bladder disorders include overactive bladder, hypertrophied bladder neck and detrusor hyperreflexia, for example. Exemplary prostate disorders include benign prostatic hyperplasia, prostatitis and prostate cancer. An additional example of a cholinergically-influenced disorder is hyperhidrosis and the surface area of the patient, when treated accordingly, can is selected from the group consisting of an axillary skin surface area, a palmar skin surface area and a plantar skin surface area.

A method for treating a patient suffering from cholecystitis is also herein described, which can comprise the steps of administering a first composition containing an extracellular matrix digesting enzyme to a gall bladder surface area of the patient, allowing sufficient time to pass for the extracellular matrix digesting enzyme to diffuse through the gall bladder surface area, administering a second composition containing a botulinum toxin to the gall bladder surface area and allowing sufficient time for the botulinum toxin to diffuse through the gall bladder surface area to alleviate at least one symptom associated with cholecystitis, thereby treating the patient suffering from cholecystitis. Optionally the first composition can be removed after the sufficient amount of time has passed, and similarly, the second composition can also be optionally removed after a sufficient amount of time has passed.

The gall bladder surface area can be within the gall bladder proper and/or within a duct of the gall bladder, and useful botulinum toxins can be selected from the group consisting of botulinum toxin type A, B, $C_1$, D, E, F and G. For example, where the botulinum toxin is a botulinum toxin type A, it can be administered in an amount from between about 1 unit to about 3000 units. Where the administered botulinum toxin is botulinum toxin type B it can be administered in an amount from about between 50 units to about 25,000 units. Useful extracellular matrix digesting enzymes are selected from the group consisting of a hyaluronidase, a tissue plasminogen activator and a collagenase.

Symptoms associated with cholecystitis, and which can be alleviated in accordance with the presently disclosed methods can include gall bladder wall inflammation, intense pain in the upper abdominal region that steadily increases, pain in the back, ordinarily between the shoulder blades, or pain under the right shoulder, pain in the lower region of the stomach, near the pelvis, and nausea and vomiting. Additional symptoms can also include abdominal bloating, intolerance of fatty foods, belching, gas, and indigestion. Symptoms may most often be felt after a fatty meal and at night. The cholecystitis can be due to the presence of at least one gall stone.

In a particular embodiment, a method that excludes injection of the botulinum toxin or an extracellular matrix digesting enzyme for administering a botulinum toxin to a patient suffering from cholecystitis can comprise the steps of accessing a gall bladder of the patient suffering from cholecystitis and administering a first composition containing at least one extracellular matrix digesting enzyme to a gall bladder surface area of the patient and then administering the second composition containing a botulinum toxin to the gall bladder surface area of the patient, such that the first composition containing at least one extracellular matrix digesting enzyme and the second composition containing a botulinum toxin are instilled into the gall bladder and/or a duct of the gall bladder, in order to contact a gall bladder surface area of the patient. As above, useful botulinum toxin types include A, B, $C_1$, D, E, F and G. For botulinum toxin type A, an exemplary range of dosage can be between about 10 units and about 2750 units.

In still another aspect, method disclosed herein provide for sufficient dilation of the duct of the gall bladder, subsequent to instillation of the first composition containing at least one extracellular matrix digesting enzyme and the second composition containing a botulinum toxin, to allow a gall stone to pass through the duct of the gall bladder and thus avoid surgical removal of the stone. In one instance, the at least one extracellular matrix digesting enzyme is a hyaluronidase and the botulinum toxin is a botulinum toxin type A.

In particular embodiments, in addition to reducing the number of injections utilized to treat cholinergically-influenced disorders, the method for administering a neurotoxin to a patient in need thereof can specifically exclude any injection of the neurotoxin or an extracellular matrix digesting enzyme, where the method comprises the steps of administering a first composition containing at least one extracellular matrix digesting enzyme onto a skin surface area or luminal surface area of the patient and administering the second composition containing a neurotoxin onto the skin surface area or luminal surface area of the patient, where the neurotoxin diffuses to a greater extent that if administered without the first composition containing at least one extracellular matrix digesting enzyme, and further the administration excludes injection of both the first and second compositions. In such embodiments, the skin surface area can be an axillary skin surface area, plantar skin surface area or palmar skin surface area. An exemplary luminal surface area can be a bladder luminal surface area, a urethral luminal surface area, a nasal luminal surface area or a prostate luminal surface area.

For example, in methods that specifically exclude injection of the neurotoxin or an extracellular matrix digesting enzyme, the administration of one or both of the extracellular matrix digesting enzyme and botulinum toxin is achieved by application via at least one of spraying or rubbing onto the skin surface area or luminal surface area of the patient. A method can further include the step of drying the skin surface after administration of the first composition (containing at least one extracellular matrix digesting enzyme) to the skin surface. Drying the skin surface can include the step of allowing sufficient time to pass to allow evaporation of the first composition from the skin surface, before commencing with administration of the second composition (containing a neurotoxin, such as a botulinum toxin selected from the group consisting of botulinum toxin type A, B, $C_1$, D, E, F or G), onto the skin surface area.

Another non-injection method is provided in accordance with the instant disclosure, for treating a urologic disorder in a patient in need thereof, comprising the steps of instilling a first composition containing hyaluronidase into to a bladder of the patient in order to contact a bladder luminal surface area (which has a glycosaminoglycan layer) to the first composition and maintaining the first composition within the bladder to allow sufficient time to pass such that the introduced (and instilled) hyaluronidase interacts with the glycosaminoglycan layer and diffuses through the bladder luminal surface area, optionally draining the first composition from the bladder, instilling a second composition containing a botulinum toxin type A to the bladder in order to contact the bladder luminal surface area previously contacted by the previously instilled and removed first composition, and retaining the instilled second composition for a sufficient time within the bladder so that a sufficient amount of botulinum toxin type A diffuses through the bladder luminal surface area to at least one layer of the muscularis propria (at least one of the a inner longitudinal, middle circular, and outer longitudinal layers) and optionally draining the second composition from the bladder, thereby alleviating at least one symptom associated with the urologic disorder and treating the urologic disorder of the patient in need thereof. It is further contemplated that a single composition/mixture that includes both an extracellular matrix digesting enzyme and a botulinum toxin therein can be instilled into a bladder.

Exemplary urologic disorders that can be so treated, that is, by methods that do not require the use of injections, include urologic disorders selected from the group consisting of overactive bladder, hypertrophied bladder neck and detrusor hyperreflexia, for example.

Each and every feature described herein, and each and every combination of two or more of such features, is included within the scope of the present invention provided that the features included in such a combination are not mutually inconsistent.

DESCRIPTION

The present disclosure provides methods by which various cholinergically-influenced disorders, such as urologic disorders and hyperhidrosis can be treated. Urologic disorders include overactive bladder, hypertrophied bladder neck and detrusor hyperreflexia, for example, which can be treated by utilizing an extracellular matrix digesting enzyme in conjunction with a neurotoxin, such as botulinum toxin as taught herein. Such use enhances the diffusion of botulinum toxin and as such can reduce, and even eliminate, the need for injection protocols that are typically utilized when treated these disorders with botulinum toxin.

In accordance with the present disclosure, the methods are described herein that take advantage of the synergistic effect of utilizing at least one extracellular matrix digesting enzyme in conjunction with a neurotoxin, preferably a botulinum toxin, in order to treat various disorders, as more fully described below. An advantageous aspect of the methods detailed herein is the reduction in the number of, and even elimination of, injections to administer therapeutically effective amounts of the neurotoxin to the patient and thereby treat the disorder.

The neurotoxin can be formulated in any pharmaceutically acceptable formulation/formulations such as a liquid, powder, cream, emulsion, suspensions, solutions, and the like.

The amount of the Clostridial toxin, such as botulinum toxin administered according to a method within the scope of the disclosed herein can vary according to the particular characteristics of the disorder being treated, for example, such a urologic disorder or hyperhidrosis, including the severity and other various patient variables including size, weight, age, and responsiveness to therapy, as known in the art. To guide the practitioner, typically, no less than about 1 unit and no more than about 2500 units of a botulinum toxin type A (such as BOTOX®) is administered per injection site if the toxin is injected, per patient treatment session. For a botulinum toxin type A such as DYSPORT®, no less than about 2 units and no more about 4000 units of the botulinum toxin type A are administered per injection site, per patient treatment session, if injected. For a botulinum toxin type B such as MYOBLOC®, no less than about 40 units and no more about 25,000 units of the botulinum toxin type B are administered per injection site, per patent treatment session. Similar amounts of toxin can be utilized in accordance with methods that do not utilize injection of toxin, such as instillation, swabbing or spraying of neurotoxin containing compositions to areas to which a composition containing an extracellular matrix digesting enzyme has been or is/will be administered, either by injection or non-injection. Of course, the amount of neurotoxin and extracellular matrix containing enzyme to be utilized in a particular patient to treat a particular disorder/condition will be determined by the attending physician, as known in the medical arts. For example, when treating a urologic disorder by administration of neurotoxin to a patient's bladder, the volume of the solution/dispersion and concentration of the neurotoxin may depend upon the size of the patient, the severity of the disorder, thickness of the bladder wall, concentration/amount of administered extracellular matrix digesting enzyme and muscle, comorbidities, and other factors.

For example, if treating a patient suffering from hyperhidrosis, such as axillary hyperhidrosis, the hyperhidrotic surface area to be treated (here an armpit) is first determined by conducting a simple Minor's starch and iodine test, in order to determine the area to be treated. The area is demarcated, and a composition containing an extracellular matrix digesting enzyme, such as a solution containing hyaluronidase, is applied to the hyperhydrotic area. For example, the composition so applied can contain about 150 U of hyaluronidase and is left on the patient's skin surface to allow the hyaluronidase to be absorbed. Such application can be simply accomplished by brushing, spraying or swabbing a first composition containing an extracellular matrix digesting enzyme onto the desired area. In some instances, sufficient time is allowed to pass to allow the skin surface area to dry. Subsequently, a composition that contains a neurotoxin, such as a botulinum toxin, is applied to the area. Such a composition can contain, for example, from about 50 to about 200 units of a botulinum toxin. Preferably, the composition containing the botulinum toxin is similarly brushed, sprayed or swabbed to the surface area to be treated and the patient can report a decrease in excessive sweating and a return to euhidrosis in about 2 to about 7 days time.

Alternatively, for example, the botulinum toxin can be administered by injection, such as by subdermal injection. However, due to the topical application of the extracellular matrix digesting enzyme, such as hyaluronidase, the number of necessary injections is greatly reduced as compared to the typical number of injections of botulinum toxin utilized to treat axillary hyperhidrosis. As an example, between about 5 to about 10 injection sites, having between about 5 to about 25 units of BOTOX® (botulinum toxin type A) at each site, can be administered to the area to which the extracellular matrix digesting enzyme is administered. Preferably, up to about 5 injections of botulinum toxin are administered to the area to which the extracellular matrix digesting enzyme is administered. Typically, the injections are evenly spaced from one another to as to cover the maximum amount of hyperhidrotic area.

In another example, the methods disclosed herein provide for methods to treat various urological disorders, for example, by administering a neurotoxin such as a botulinum toxin to a bladder's luminal surface area to which has been administered a composition that contains an extracellular matrix digesting enzyme. Access to the lumen of the bladder is easily accomplished by insertion of a catheter or cannula into the urethra and to the bladder, as known in the art. Once the catheter is so positioned, between 1 and 1000 ml of a first composition containing extracellular matrix digesting enzyme, such as hyaluronidase, is instilled into the bladder. The solution can contain anywhere from about 25 to about 50 Units of hyaluronidase, the volume of the composition (for example a solution) and concentration of the hyaluronidase may depend upon the size of the patient, thickness of the bladder wall and muscle, comorbidities, severity of the urologic disorder, weight of the patient among other standard factors considered in the medical arts when determining appropriate dosages/parameters for treating particular patients. The first composition may then be drained from the bladder after allowing a sufficient amount of time to pass, such as from about 5 minutes to about 2 hours. In some embodiments, where, for example, from about 10 ml to about 50 ml of the first composition is instilled into the bladder, there may not be a need to drain the bladder, as the composition can be absorbed. During this time, the patient may be positioned (turned on their sides, onto their stomach and back) in order to thoroughly establish contact of the first composition with the bladder luminal surface. The first composition can then be drained from the bladder (utilizing known drainage techniques, and can include external, manual depression of the bladder, for example). Subsequently, a second composition containing a neurotoxin, preferably a botulinum toxin, most preferably a botulinum toxin type A, is then administered by instillation into the bladder to contact the bladder luminal surface previously administered the first composition containing the extracellular matrix digesting enzyme. From about 25 to about 3000 units, more preferably from about 100 to about 2500 units of a botulinum toxin type A can be so instilled, and from about 500 to about 50,000 units, and more preferably from about 1000 to about 25,000 units of a botulinum toxin type B can be so instilled into the bladder or a clinically equivalent amount for other botulinum toxin serotypes, as known to the skilled person in the art.

The dosage of neurotoxin agent that is intravesically administered to the patient is one that is therapeutically effective to achieve the desired treatment outcome. In the case of botulinum toxin, the typical dose administered to the patient may be any dose less than a toxic dose (for example less than 3000 units of BOTOX®, a botulinum toxin type A, for a 70 kg man), for example between 1 and 1,500 units and more preferably between 50 and 500 units per patient per treatment, although smaller or larger doses may be administered as required. The doses can be given as a single dose, or as divided doses over a span of time, such as over a period of days or weeks or months, depending on the length of effect for a given neurotoxin preparation.

Similar to the first composition, between about 1 and about 1000 ml of the second composition containing botulinum toxin can be instilled into the bladder and the patient placed in various positions as detailed above. Because the patient will likely be instructed to empty his or her bladder prior to the procedure, the bladder will likely not be full or markedly distended. In particular embodiments, instillation of about 1 to about 100 mls of solution/dispersion, and more preferably 10-50 ml of solution/dispersion, may be sufficient to coat the inside of the bladder (bladder luminal surface). Additionally, after a sufficient amount of time (e.g. from about 5 minutes to about 2 hours) has passed after instillation of the second composition into the bladder, the second composition containing the botulinum toxin can be drained from the bladder, although if a smaller volume of the second composition is instilled (e.g. from about 1 to about 10 mls), the attending physician may not desire to drain the bladder and rather allow for the second composition to be naturally drained (expelled) by the patient. A composition (containing either/or a botulinum toxin or an extracellular matrix digesting enzyme) for bladder infusion according to the teaching of the present disclosure typically is of a volume of about 80 to about 100 ml, and more preferably 80 ml. Of course, the attending physician can increase or decrease the concentration of the neurotoxin containing composition and extracellular matrix digesting enzyme composition, and volume of the instilled compositions, in accordance with the patient's bladder size (children and young adults having smaller bladders than adults) and severity of the disorder treated.

Draining of the instilled compositions can be accomplished via catheter or naturally expelled, appropriate care being taken, of course, associated with the disposable of neurotoxin containing compositions. Within about 2 to about 7 days the patient can report urological improvement and even a return towards a normal urological state, which, for an adult, is having a flow rate of about 25 cc/sec and a void volume of about 400 cc.

Draining of the first composition (containing the extracellular matrix digesting enzyme) and the second composition are described above for instillation into a bladder. If instilled into a portion of a patient's GI tract or into a nasal lumen, appropriate routes of removal/drainage can be employed, such as simply tilting/positioning the patients head to instill or remove compositions from a nasal luminal surface area, for example.

An exemplary method for intravesically administering the first and second compositions utilizes a urinary catheter that extends through the urethra into the bladder. The catheter may be a "straight catheter" with a single lumen (simply a straight channel) or alternatively might be a catheter that in some cases uses a balloon or other mechanism to fix the catheter within the bladder (such as a Foley catheter). Standard sizes for such a catheters are known in the art, such as 10-16 French (3-5 mm), though larger or smaller sizes might be used depending on size the patient and his or her anatomy.

Once the catheter is in place, typically between 1 and 1000 ml of solution/dispersion containing neurotoxin and more preferably in the range of 10-50 ml of solution/dispersion containing neurotoxin can be instilled through the catheter into the bladder. The volume of the solution/dispersion and concentration of the neurotoxin may depend upon the size of the patient, thickness of the bladder wall and muscle, comorbidities, and other factors.

Another representative means of intravesically administering the neurotoxin involves the placement of a suprapubic needle or catheter through the abdominal wall directly into the patient's bladder. This is a more invasive method and is not the preferred method of access to the bladder; however, due to urethral tract infections, obstructions, etc. may be the best route that is available to the attending physician to access the bladder luminal surface. The required volume of compositions containing the extracellular matrix digesting enzyme and the neurotoxin can then be introduced into the bladder, either using direct vision, endoscopic or fluoroscopic guidance, as known in the art. Intravesical administration in accordance with the present disclosure can also be accomplished utilizing a cystoscope which facilitates viewing of intravesical delivery of the compositions. Here, the compositions can be introduced into the bladder lumen through the working channel of the cystoscope or through a catheter or other tubular structure passed within or alongside the cystoscope.

In some cases, the urethra or suprapubic catheter/needle may have an inflatable component that can be inflated within the bladder to "lock" the urethra or suprapubic catheter/needle in place and prevent its removal. Inflating the balloon or other inflatable device takes up volume within the bladder, and can thereby require less of the extracellular matrix digesting enzyme composition and neurotoxin containing composition to be administered.

In accordance with once aspect, the extracellular matrix digesting enzyme and a botulinum toxin can be serially administered or administered at the same time. An exemplary mixture for instillation or spreading to a surface area in can, for, example, containing 100 units of botulinum toxin type A (BOTOX) diluted with 9 ml of preserved saline and 1 ml of hyaluronidase (1500 units, here HYALASE).

Although examples of routes of administration and dosages are provided, the appropriate route of administration and dosage are generally determined on a case by case basis by the attending physician. Such determinations are routine to one of ordinary skill in the art (see for example, Harrison's Principles of Internal Medicine (1998), edited by Anthony Fauci et al., 14th edition, and published by McGraw Hill). For example, the route and dosage for administration of a Clostridial neurotoxin, such as a botulinum toxin, according to the present disclosed invention can be selected based upon criteria such as the solubility characteristics of the neurotoxin chosen as well as the intensity of the disorder treated.

The following examples provide those of ordinary skill in the art with specific preferred methods to practice methods that are within the scope of the present invention and are not intended to limit the scope of the invention.

EXAMPLES

Example 1

A 64-year old patient has an overactive bladder, and as a result has urge and stress incontinence. He unfortunately experiences from about 5-8 leakage accidents per day, requiring necessary changes of the adult diapers that he is forced to wear because of his condition. Upon presentation to his urologist, a regimen of bladder instillation is decided upon, utilizing botulinum toxin and an extracellular matrix digesting enzyme.

The patient is asked to relieve himself before lying on his back upon an adjustable table or bed, after which a urethral catheter is inserted into his urethra and to the patient's bladder. A first composition containing an extracellular matrix digesting enzyme, here 150 USP units of nonpreserved hyaluronidase (such as HYLENEX) in 50 mls of nonpreserved saline, are instilled into the man's bladder. The catheter is then removed and the surface upon which the patient is lying is tilted so that his head is lower than his feet, in order that the first composition contacts the bladder luminal surface at the dome of the bladder. The patient remains in such a position for 10 minutes, after which he is titled forward so that his feet are lower than his head so that the first composition is now in full contact with the floor of the bladder. The patient remains so for 10 more minutes, and is then asked to roll onto his left and right sides (for 10 minutes each, respectively) and then onto his stomach, to more fully expose all of the bladder's lateral luminal surface areas to the first composition that includes the an extracellular matrix digesting enzyme. The patient is then recatheterized and stood upright, to drain the bladder. Then a second composition, which contains 500 units of a botulinum toxin type A, such as BOTOX® reconstituted in 50 mls of non-preserved saline, is then instilled into the patient's bladder and the patient is then subjected to the same positioning regimen as for the first composition. Subsequently, the patient is drained of the second composition and discharged.

Weekly follow up visits show that the patient now has control over his urination, and although he still wears adult diapers out of abundance of caution, and does not have accidental leakage episodes since the installation treatment and can enjoy running and other physical activities that his stress incontinence forces him to avoid.

Example 2

A 72-year old man has suffers from urge incontinence due to a neurogenic bladder dysfunction that is secondary to his Parkinson's disease. His condition forces the patient to make, on average, over 20 trips to the restroom per day to relieve his bladder. The situation is presented to his physician and administration of an extracellular matrix digesting enzyme and botulinum toxin to his bladder walls is decided upon.

The patient is firstly asked to relive himself before insertion of an appropriately sized catheter (3-5 mm) into his urethra. A first composition containing 300 USP units of nonpreserved hyaluronidase (such as HYLENEX) in 2 mls of solution is instilled into the bladder and a positioning routine, however the patient now remains in the various positions for 5 minutes. After drainage of the patient's bladder, a cytoscope is utilized to inject botulinum toxin at one site into each of the dome, dorsal, ventral and lateral walls of the bladder, sparing the trigone. Thus a total of five injections, of about 10 units of a botulinum toxin type A complex at each injection site for a total of about 50 units of botulinum toxin type A (e.g. BOTOX®, or about 40 units of DYSPORT® at each site, for a total of 200 units of botulinum toxin type A) are so delivered, a great reduction from the typically 20-40 injections of prior methods which utilizing toxin alone. The instillation of the extracellular matrix digesting enzyme into the bladder and to the bladder luminal surface facilitates the greater diffusion of the toxin throughout the muscularis propria (i.e. the three layers: inner longitudinal, middle circular, and outer longitudinal muscles of the bladder's muscular layer) while reducing the amount of injections that need to be performed.

The patient rests after the procedure is completed and is then taken home. During follow-up visits, the patient reports no unwanted systemic or local side effects and shows an improvement in bladder function, both subjectively (reduction in urgency to urinate) and objectively (now only urinates 4 times/day on average).

Injection of up to 5000 units of botulinum toxin type B, at 1000 units per injection site can also be performed and treats neurogenic bladder dysfunction that is secondary to his Parkinson's disease, similarly.

Example 3

A 58 year old woman suffers urinary retention that is secondary to spastic sphincter and has a hypertrophied bladder neck. The patient typically urinates only 2-3 times per week and when so doing only manages to void approximately 50 mls of urine per visit to the restroom. Her caretaker fears resultant high intravesical pressure and reduction in bladder capacity will result in deterioration of the upper urinary tract.

Accordingly, her urologist inserts a cytoscope and flexible endoscopic needle into her urethra and into the bladder. A first composition comprising a total of 100 units of hyaluronidase, such as VITRASE, is injected into the detrusor muscle, at a total of 10 sites, 2 sites into each into of the dorsal, ventral and lateral bladder walls (for a total of 8 injections to the bladder walls) and 2 sites into the bladder neck and the cytoscope removed. After 10 minutes, a second composition of 100 mls of nonpreserved saline, containing 750 units of a botulinum toxin type A (e.g. DYSPORT®) is instilled into bladder and kept there for 30 minutes, after which the patent is recatherized and voided of the second composition. Within 7 days, the caretaker reports improved frequency of urination (1 to 2 times per day) and an increase in the amount of urine voided (about 300 to 400 mls per visit to the restroom).

Example 4

A 23 year old college student reports to her dermatologist stating that her excessive axillary sweating is rendering her very self conscience and as a result her grades are suffering and she has become more and more introverted as time passes. The dermatologist determines that the patient is suffering from hyperhidrosis and suggests utilizing a neurotoxin to treat the hyperhidrosis since roll-on antiperspirants have no effect on her excessive sweating.

After wiping the axilla of the patient dry with a paper towel, a Minor's iodine-starch test is performed to demarcate the hyperhidrotic skin surface area to be treated (such as by utilizing a vegetable-based ink). Applied to this axillary skin surface area is a first composition that contains an extracellular matrix digesting enzyme, here 1 ml containing 150 USP units of nonpreserved hyaluronidase (such as HYLENEX) is applied by swabbing the demarcated area with an applicator, such as a cotton swab. The area is then allowed to air-dry, for about 10 minutes. Thereafter and to the axillary skin surface area, about 25 units of botulinum toxin type A (such as BOTOX®, or about 100 units of DYSPORT®, or about 1250 units of MYOBLOC®) is applied, utilizing another cotton swab and allowed to dry. The same procedure is performed on the patient's other axilla.

Within one week, the patient reports that they no longer experience the excessive sweating that pervaded their previous days, and that there are no excessive local hypotonicity or systemic adverse effects.

A similar approach can be utilized to treat other skin surface areas that may also be hyperhidrotic, such as the palms of the hands (palmar skin surface area) and/or the soles of the feet (plantar skin surface area).

Example 5

A 42 year old single man reports to his dermatologist that his excessive axillary sweating is rendering him very self conscience to the point of no longer interacting with the opposite sex. The dermatologist determines that the patient is suffering from hyperhidrosis and suggests utilizing a neurotoxin to treat the hyperhidrosis, since all of the topical antiperspirants he as tried have not been effective.

After wiping the axilla of the patient dry with a paper towel, a Minor's iodine-starch test is performed to demarcate the hyperhidrotic skin surface area to be treated (such as by utilizing a vegetable-based ink). Applied to this axillary skin surface area is a first composition that contains an extracellular matrix digesting enzyme, here 2 mls containing 300 USP units of nonpreserved hyaluronidase (such as HYLENEX), applied by spraying the demarcated area with a spray applicator, such as a non-aerosol pump. The area is then allowed to air-dry, for about 10 minutes. Thereafter and to the axillary skin surface area, about 1000 units of botulinum toxin type B (such as MYOBLOC®) is sprayed thereon, utilizing a spray applicator and allowed to dry. The same procedure is performed on the patient's other axilla.

Within 10 days, the patient reports that he no longer experiences the excessive sweating that pervaded their previous lonely days, and further that there are no excessive local hypotonicity or systemic adverse effects. The patient reports that the procedure was effective for between about 2 to about 6 months, at which time he returns to the dermatologist for another round of treatment.

Example 6

A 15 year old high school student reports to his family physician that his hyperhidrotic hands are a source of great embarrassment. Accordingly, the doctor proceeds to perform a Minor's iodine-starch test to demarcate the areas to be treated. It appears that the excessive sweating mainly originates from the area between the patient's wrists to the bases of the fingers.

Accordingly, 1 ml of hyaluronidase containing 150 USP units is applied to the wrist to the base of the fingers (1 ml/150 USP units per hand) and allowed to dry. After drying, 4 points of injection in the palm (midline at the base of wrist, base of middle finger, and between base of the thumb and base of the index finger, and between base of the pinky and base of wrist) at which about 40 units of botulinum toxin type A (such as BOTOX®, or about 80 units DYSPORT® or 200 units of a botulinum toxin type B, such as MYOBLOC®) is injected intradermally at each of the four points.

After 5 days, the teen reports that his palms are not longer sweaty and there are no reports of excessive hypotonicity or systemic effects. The hyperhidrosis abates for up to 8 months, at which time the teen returns to have the procedure repeated. If needed, the treatment is also applied to the ventral portions of the patient's fingers, if exhibiting excessive sweating.

Example 7

A 76 year old man suffers from chronic urinary retention due to the enlargement of his prostate due to benign prostatic hyperplasia. It is decided by his physician that the patient undergo administration of a botulinum toxin to the prostate in order to alleviate his urinary retention and treat the benign prostatic hyperplasia. In order to minimize the number of injections of botulinum toxin to the prostate, an extracellular matrix enzyme, such as hyaluronidase, is injected into the transition zone of the lateral lobes of the prostate and the median lobe. Three injections of hyaluronidase (50 units at injection point) are made utilizing an injection cytoscope and a 23 gauge needle, one injection into each of the lateral lobes and one injection into the median lobe. After 5 minutes, three injections of a botulinum toxin type A are similarly administered, where each injection contains 50 units of botulinum toxin type A (BOTOX®) for a total of 150 units.

After about 7 days, the patient reports an improvement in spontaneous voiding after this treatment and decrease post voiding residual volume and pressure are decreased. These beneficial effects are maintained for about 5 months in this particular patient and no adverse effects are reported. A type B botulinum toxin can also be utilized, for example, from about 250 units to 1000 units per injection site.

Example 8

A 53 year old woman suffers from recurring bouts of pain the upper abdominal region. The pain steadily increases over time (over about 15 minutes to an hour) and sometimes is accompanied by pain located in her back. Upon visiting her internist, he finds that she suffers from cholecystitis as a result of the formation of gallstones. The physician decides to remove the gall stones and instill her gall bladder utilizing a combination of an extracellular matrix digesting enzyme (hyaluronidase) and botulinum toxin type A, utilizing common endoscopic retrograde cholangiopancreatography (ERCP) techniques to gain access to her gall bladder.

After sedation of the patient, a flexible camera (endoscope) is inserted through her mouth, eventually through the pylorus and into her duodenum where the ampulla of Vater (the opening of the common bile duct and pancreatic duct) exists, at which the sphincter of Odi controls the ampulla's opening. The region is directly visualized with the endoscopic camera while a plastic catheter (or cannula and the like) is inserted through the ampulla. About 25 mls of a first composition comprising a total of 100 units of hyaluronidase, such as VITRASE, is instilled into the gall bladder through the inserted catheter. After 15 minutes, any remaining first composition is removed via the same catheter. Subsequently, 25 mls of a second composition containing 200 units of botulinum toxin type A (BOTOX®) is also instilled into the gall bladder through the catheter. After another 20 minutes, any remaining second composition is then removed and the endoscope and catheter is removed. During the instillation and removal of the first and second compositions, two gall stones, having circumferences of about 6 mm and 8 mm, are flushed out and removed.

Example 9

A debilitated 78 year old man suffers from recurring bouts of pain between the shoulder blades and under the right shoulder, and his caregiver reports that he feels nauseated and vomits on occasion. Upon inspection, his primary physician notes that his gallbladder is inflamed, and since no gall stones are found, a diagnosis of acute acalculous cholecystitis is made.

His physician proceeds to instill the gall bladder, utilizing a combination of an extracellular matrix digesting enzyme (hyaluronidase) and botulinum toxin type B.

After anaesthetizing the patient, ERCP can be performed to insert a flexible camera (endoscope) through his mouth, and as in example 8, a plastic catheter (or cannula and the like) is inserted through the ampulla.

About 30 mls of a first composition comprising a total of 150 units of hyaluronidase, such as VITRASE, is instilled into the gall bladder through the inserted catheter. After 25 minutes, any remaining first composition is removed via the same catheter. Subsequently, 30 mls of a second composition containing 5000 units of botulinum toxin type B (MYOBLOC®) is also instilled into the gall bladder through the catheter. After another 30 minutes, any remaining second composition is removed and the endoscope and catheter is removed.

After the anesthetic sufficiently wears off, the patient is then sent home with his caretaker. Upon questioning at a follow up visit with his 3 months later, the caretaker reports that the man no longer suffers from any pain between the shoulder blades or under the right shoulder, and does not vomit.

Although the present invention has been described in detail with regard to certain preferred methods, other embodiments, versions, and modifications within the scope of the present invention are possible. For example, a wide variety of neurotoxins can be effectively used in the methods of the present invention in place of Clostridial neurotoxins. Additionally, the present invention includes administration of two or more different Clostridial toxin components and targeting moieties, administered concurrently or consecutively. For example, administration of a particular second composition containing botulinum toxin type A to the bladder luminal surface or hyperhidrotic skin surface area can be administered to the patient and if increased tolerance resistance to it's effect is noted, a botulinum toxin of a different serotype, such as botulinum toxin type B or F, can be utilized in subsequent applications to treat the cholinergically-influenced disorder. While this invention has been described with respect to various specific examples and embodiments, it is to be understood that the invention is not limited thereto and that it can be variously practiced with the scope of the following claims.

What is claimed is:

1. method for treating a patient suffering from cholecystitis wherein the cholecystitis is due to the presence of at least one gall stone, comprising the steps of:

a) administering either topically or by instillation a first composition containing an extracellular matrix digesting enzyme to a gall bladder surface area of the patient;
b) allowing the extracellular matrix digesting enzyme to diffuse through the gall bladder surface area for between about 5 minutes and about 2 hours;
c) administering either topically or by instillation a second composition containing a type A or B botulinum toxin to the gall bladder surface area; and
d) allowing sufficient time for the botulinum toxin to diffuse through the gall bladder surface area to alleviate at least one symptom associated with cholecystitis, thereby treating the patient suffering from cholecystitis.

2. The method of claim 1, wherein the gall bladder surface area is within a duct of the gall bladder.

3. The method of claim 1, wherein the botulinum toxin is botulinum toxin type A.

4. The method of claim 1, wherein the botulinum toxin is a botulinum toxin type B.

5. The method of claim 1, further comprising the steps of optionally removing the first composition after step (b) and optionally removing the second composition after step (d).

6. The method of claim 1, wherein the extracellular matrix digesting enzyme is selected from the group consisting of a hyaluronidase, a tissue plasminogen activator and a collagenase.

7. The method of claim 3, wherein the botulinum toxin type A administered is from between about 1 unit to about 3000 units.

8. The method of claim 4, wherein the botulinum toxin type B administered is from about 50 units to about 25,000 units.

9. A method for administering a botulinum toxin to a patient suffering from cholecystitis due to the presence of at least one gall stone, the method comprising the steps of:

a) accessing a gall bladder of the patient suffering from cholecystitis;
b) administering a first composition containing at least one extracellular matrix digesting enzyme to a gall bladder surface area of the patient; and
c) administering the second composition containing a botulinum toxin to the gall bladder surface area of the patient, wherein the first composition containing at least one extracellular matrix digesting enzyme and the second composition containing a botulinum toxin are instilled into the gall bladder or a duct of the gall bladder to contact the gall bladder surface area of the patient.

10. The method of claim 9, wherein the botulinum toxin is selected from the group consisting of botulinum toxin types A, B, $C_1$, D, E, F and G.

11. The method according to claim 9, wherein the botulinum toxin is a botulinum toxin type A.

12. The method according to claim 11, wherein the amount of botulinum toxin type A administered is between about 10 units and about 2750 units.

13. The method according to claim 7, wherein the at least one extracellular matrix digesting enzyme is selected from the group consisting of a hyaluronidase, a tissue plasminogen activator and a collagenase.

14. The method according to claim 9, wherein the duct of the gall bladder dilates sufficiently subsequent to instillation of the first composition containing at least one extracellular matrix digesting enzyme and the second composition containing a botulinum toxin to allow a gall stone to pass through the duct of the gall bladder.

15. The method according to claim 1, wherein the at least one extracellular matrix digesting enzyme is a hyaluronidase and the botulinum toxin is a botulinum toxin type A.

* * * * *